United States Patent
Chevalier et al.

(10) Patent No.: US 8,628,757 B2
(45) Date of Patent: Jan. 14, 2014

(54) OLEO-ALCOHOLIC ANHYDROUS FLUID SCREENING COMPOSITION COMPRISING A LIPOPHILIC POLYAMIDE POLYCONDENSATE

(75) Inventors: Cyril Chevalier, Juvisy-sur-Orge (FR); Aurelia Gohier, Le Mans (FR); Carole Guiramand, Jouy en Josas (FR)

(73) Assignee: L'Oreal, Paris (FR)

( * ) Notice: Subject to any disclaimer, the term of this patent is extended or adjusted under 35 U.S.C. 154(b) by 377 days.

(21) Appl. No.: 12/750,230

(22) Filed: Mar. 30, 2010

(65) Prior Publication Data

US 2010/0310481 A1 Dec. 9, 2010

Related U.S. Application Data

(60) Provisional application No. 61/202,863, filed on Apr. 14, 2009.

(30) Foreign Application Priority Data

Mar. 31, 2009 (FR) ...................................... 09 52038

(51) Int. Cl.
A61K 8/42 (2006.01)
A61Q 17/04 (2006.01)

(52) U.S. Cl.
USPC ................................ 424/59; 424/60; 424/401

(58) Field of Classification Search
USPC ............................................ 424/59, 60, 401
See application file for complete search history.

(56) References Cited

U.S. PATENT DOCUMENTS

| | | | |
|---|---|---|---|
| 3,895,104 A * | 7/1975 | Karg | ................................ 424/59 |
| 4,731,242 A | 3/1988 | Palinczar | |
| 6,592,857 B2 | 7/2003 | Lawson et al. | |
| 2005/0197479 A1 | 9/2005 | Pavlin | |
| 2006/0204461 A1 * | 9/2006 | Pavlin | .............................. 424/64 |
| 2008/0115846 A1 | 5/2008 | Josso et al. | |
| 2008/0233065 A1 * | 9/2008 | Wang et al. | ...................... 424/64 |
| 2009/0016971 A1 | 1/2009 | Gaudry et al. | |
| 2009/0035243 A1 * | 2/2009 | Czarnota et al. | ................. 424/64 |

FOREIGN PATENT DOCUMENTS

| | | |
|---|---|---|
| EP | 1813266 A1 | 8/2007 |
| FR | 2897265 A1 | 8/2007 |
| FR | 2918563 A1 | 1/2009 |
| WO | WO-0247620 A2 | 6/2002 |

OTHER PUBLICATIONS

Reference Todorov (Smart Skin Care. Chemical UVA sunscreen/sunblock agent: Avobenzone copyright 1999-2012).*
IUPAC Adduct definition (PAC, 1994, 66, 207-2284. Glossary of terms used in physical organic chemistry, p. 1082 (IUPAC Recommendations 1994), doi:10.1351/pac199466051077).
Opposition by Croda International Plc in counterpart EP patent 2236173 dated May 29, 2013.

* cited by examiner

Primary Examiner — Anoop Singh
Assistant Examiner — Anna Falkowitz
(74) Attorney, Agent, or Firm — Novak Druce Connolly Bove + Quigg LLP

(57) ABSTRACT

The present invention relates to an anhydrous fluid composition comprising, in a cosmetically acceptable medium:
a) at least one hydrocarbon oil and
b) at least one lipophilic organic UV screening agent and
c) at least one linear $C_1$-$C_3$ monoalcohol, in particular ethanol, and
d) at least one lipophilic polyamide polycondensate.

The present invention also relates to the use of the said composition in the manufacture of products for the cosmetic treatment of the skin, nails, hair, eyelashes, eyebrows and/or scalp, in particular care products, sun protection products, makeup products or scenting products.

17 Claims, No Drawings

OLEO-ALCOHOLIC ANHYDROUS FLUID SCREENING COMPOSITION COMPRISING A LIPOPHILIC POLYAMIDE POLYCONDENSATE

CROSS REFERENCE TO RELATED APPLICATIONS

This application claims priority to FR 0952038 filed Mar. 31, 2009 and claims benefit of U.S. Provisional Application No. 61/202,863 filed Apr. 14, 2009, the entire contents of all are hereby incorporated by reference.

The present invention relates to an anhydrous fluid composition comprising, in a cosmetically acceptable medium:
a) at least one hydrocarbon oil and
b) at least one lipophilic organic UV screening agent and
c) at least one linear $C_1$-$C_3$ monoalcohol and
d) at least one lipophilic polyamide polycondensate.

It is known that light radiation with wavelengths of between 280 nm and 400 nm makes possible browning of the human epidermis and that rays with wavelengths more particularly of between 280 and 320 nm, known under the name UV-B rays, cause erythemas and skin burns which may be harmful to the development of natural tanning. For these reasons, and for aesthetic reasons, there exists a constant demand for means for controlling this natural tanning for the purpose of thus controlling the colour of the skin; it is thus advisable to screen out this UV-B radiation.

It is also known that UV-A rays, with wavelengths of between 320 and 400 nm, which cause browning of the skin, are capable of bringing about a detrimental change in the latter, in particular in the case of sensitive skin or of skin continually exposed to solar radiation. UV-A rays cause in particular a loss in elasticity of the skin and the appearance of wrinkles, resulting in premature skin ageing. They promote the triggering of the erythema reaction or accentuate this reaction in some subjects and can even be the cause of phototoxic or photoallergic reactions. Thus, for aesthetic and cosmetic reasons, such as the preservation of the natural elasticity of the skin, for example, more and more people desire to control the effect of UV-A rays on their skin. It is therefore desirable also to screen out UV-A radiation.

With the aim of providing protection of the skin and keratinous substances against UV radiation, use is generally made of sun compositions comprising organic screening agents which are active in the UV-A region and which are active in the UV-B region.

Numerous cosmetic compositions intended for the photoprotection (UV-A and/or UV-B) of the skin have been provided to date. The aim is very particularly to find fluid formulations which provide the users with ready application on the skin.

Among the fluid sun compositions provided to date, the anhydrous formulations of sun oil type are particularly sought for due to their ready and pleasant application on the skin and their good resistance to water. However, they are not very widespread in the market of sun products as it is difficult to obtain a sun protection factor of greater than 10 and a UV-A protection factor corresponding to the ratio required by the various regulations with regard to sun products, in particular of greater than 5.

The sun protection factor (SPF) is expressed mathematically by the ratio of the irradiation time necessary to reach the erythemogenic threshold with the UV screening agent to the time necessary to reach the erythemogenic threshold without UV screening agent. It is evaluated in vivo in particular according to the International Method published by Colipa/CTFA SA/JCIA (May 2006).

For the characterisation of the protection with respect to UV-A radiation, the PPD (Persistent Pigment Darkening) method, which measures the colour of the skin observed 2 to 4 hours after exposure of the skin to UV-A radiation, is particularly recommended and used. This method was adopted in 1996 by the Japanese Cosmetic Industry Association (JCIA) as official test procedure for the UV-A labelling of products and is frequently used by test laboratories in Europe and the United States (Japan Cosmetic Industry Association Technical Bulletin. Measurement Standards for UVA Protection Efficacy. Issued Nov. 21, 1995 and effective of Jan. 1, 1996).

The protection factor UV-$A_{PPD}$ (UV-$A_{PPD}$ PF) is expressed mathematically by the ratio of the dose of UV-A radiation necessary to reach the pigmentation threshold with the UV screening agent ($MPPD_p$) to the dose of UV-A radiation necessary to reach the pigmentation threshold without UV screening agent ($MPPD_{np}$).

$$UV - A_{PPD}PF = \frac{MPPD_p}{MPPD_{np}}$$

Specifically, the main difficulties encountered in the manufacture of sun oils in attempting to increase the sun protection factors are to simultaneously obtain a fluid, transparent and stable formulation having a pleasant cosmetic quality.

Provision has already been made, in Applications EP 1813266 and EP 2014277, to use, in fluid aqueous sun compositions of the emulsion type, lipophilic polyamide polycondensates, in particular an ester-terminated poly(ester-amide) (ETPEA) polymer or a tertiary-amide-terminated polyamide (ATPA) polymer, in order to obtain high sun protection factors.

During its research studies, the Applicant Company has found that, on using this type of lipophilic polyamide polycondensate in a fluid anhydrous sun composition of the sun oil type, the formulation did not remain fluid and became excessively thick (formation of a gel) and of little cosmetic value. Furthermore, during storage, after 2 months, the formulation thus obtained had a tendency to become heterogeneous with exudation of oil: mixture of gelled and ungelled parts.

The need thus exists to find novel transparent fluid anhydrous sun compositions which are stable over time and which make it possible to achieve higher sun and UV-A protection factors.

In point of fact, the Applicant Company has now just discovered, surprisingly, that this objective could be achieved with an anhydrous fluid composition comprising, in a cosmetically acceptable medium:
a) at least one hydrocarbon oil and
b) at least one lipophilic organic UV screening agent and
c) at least one linear $C_1$-$C_3$ monoalcohol and
d) at least one lipophilic polyamide polycondensate.

This discovery forms the basis of the present invention.

The present invention thus relates to an anhydrous fluid composition comprising, in a cosmetically acceptable medium:
a) at least one hydrocarbon oil and
b) at least one lipophilic organic UV screening agent and
c) at least one linear $C_1$-$C_3$ monoalcohol and
d) at least one lipophilic polyamide polycondensate.

Other characteristics, aspects and advantages of the invention will become apparent on reading the detailed description which will follow.

"Cosmetically acceptable" is understood to mean compatible with the skin and/or its superficial body growths, exhibiting a pleasant colour, a pleasant odour and a pleasant feel, and not causing unacceptable discomfort (smarting, tightness, redness) liable to dissuade the consumer from using this composition.

"Fluid composition" is understood to mean, within the meaning of the invention, a composition which does not exist in a solid form and which has a viscosity, measured using a Rheomat 180 viscometer at 25° C. at the rotational speed of 200 rpm after rotating for 30 seconds, of less than 0.5 Pa·s and more preferably of less than 0.2 Pa·s and more particularly ranging from 0.0001 Pa·s to 0.1 Pa·s.

"Anhydrous composition" is understood to mean a composition comprising less than 1% by weight of water, indeed even less than 0.5% of water, and in particular devoid of water, the water not being added during the preparation of the composition but corresponding to the residual water contributed by the mixed ingredients.

"Liquid fatty phase" is understood to mean, within the meaning of the present application, a fatty phase which is liquid at ambient temperature (25° C.) and atmospheric pressure (760 mmHg) and which is composed of one or more fatty substances which are liquid at ambient temperature, also known as oils, and which are compatible with one another.

"Lipophilic" is understood to mean any cosmetic or dermatological compound capable of being completely dissolved in the molecular state in a liquid fatty phase or else of being dissolved in the colloidal form (for example in the micelle form) in a liquid fatty phase.

"Oil" is understood to mean a fatty substance which is liquid at ambient temperature (20 to 25° C.).

"Hydrocarbon oil" is understood to mean any oil predominantly comprising carbon and hydrogen atoms and optionally ester, ether, fluorinated, carboxylic acid, alcohol, silicone, amine, phenyl and/or amino acid groups.

Lipophilic Polyamide Polycondensate

"Polycondensate" is understood to mean, within the meaning of the invention, a polymer obtained by polycondensation, namely by chemical reaction, between monomers having different functional groups chosen in particular from acid, alcohol and amine functional groups.

"Polymer" is understood to mean, within the meaning of the invention, a compound having at least 2 repeat units, preferably at least 3 repeat units and better still 10 repeat units.

The lipophilic polyamide polycondensate or polycondensates are preferably present in the compositions of the invention in concentrations ranging from 0.1 to 15% by weight, with respect to the total weight of the composition, more preferably from 1 to 8% by weight.

The lipophilic polyamide polycondensates can in particular be chosen from the polyamide polymers comprising a) a polymeric backbone having hydrocarbon repeat units provided with at least one nonpendent amide unit and optionally b) at least one optionally functionalized pendent fatty chain and/or at least one optionally functionalized end fatty chain which comprise at least four carbon atoms and which are bonded to these hydrocarbon units.

The term "functionalized chains" is understood to mean, within the meaning of the invention, an alkyl chain comprising one or more functional or reactive groups chosen in particular from amide, hydroxyl, ether, oxyalkylene or polyoxyalkylene, halogen, including fluorinated or perfluorinated groups, ester, siloxane and polysiloxane groups. In addition, the hydrogen atoms of one or more fatty chains can be replaced at least partially by fluorine atoms.

The term "hydrocarbon repeat units" is understood to mean, within the meaning of the invention, a unit comprising from 2 to 80 carbon atoms and preferably from 2 to 60 carbon atoms, carrying hydrogen atoms and optionally oxygen atoms, which can be saturated or unsaturated and linear, branched or cyclic. These units each additionally comprise at least one amide group which is advantageously nonpendent and which occurs in the polymeric backbone.

Advantageously, the pendent chains are directly bonded to at least one of the nitrogen atoms of the polymeric backbone.

The lipophilic polyamide polycondensate can comprise, between the hydrocarbon units, silicone units or oxyalkylene units.

In addition, the lipophilic polyamide polycondensate of the composition of the invention advantageously comprises from 40 to 98% of fatty chains, with respect to the total number of the amide units and fatty chains and better still from 50 to 95%.

Preferably, the pendent fatty chains are bonded to at least one of the nitrogen atoms of the amide units of the polymer. In particular, the fatty chains of this polyamide represent from 40 to 98% of the total number of the amide units and fatty chains and better still from 50 to 95%.

Advantageously, the lipophilic polyamide polycondensate exhibits a weight-average molecular weight of less than 100 000 (in particular ranging from 1000 to 100 000), especially of less than 50 000 (in particular ranging from 1000 to 50 000) and more particularly ranging from 1000 to 30 000, preferably from 2000 to 20 000 and better still from 2000 to 10 000.

The lipophilic polyamide polycondensate is insoluble in water, in particular at 25° C. It especially does not comprise an ionic group.

Mention may be made, as preferred lipophilic polyamide polycondensates which can be used in the invention, of polyamides branched by pendent fatty chains and/or end fatty chains having from 6 to 120 carbon atoms and better still from 8 to 120 carbon atoms and in particular from 12 to 68 carbon atoms, each end fatty chain being bonded to the polyamide backbone via at least one bonding group L. The bonding group L can be chosen from ester, ether, amine, urea, urethane, thioester, thioether, thiourea and thiourethane groups. Preferably, these polymers comprise a fatty chain at each end of the polyamide backbone.

These polymers are preferably polymers resulting from a polycondensation between a dicarboxylic acid having at least 32 carbon atoms (having in particular from 32 to 44 carbon atoms) and an amine chosen from diamines having at least 2 carbon atoms (in particular from 2 to 36 carbon atoms) and triamines having at least two carbon atoms (in particular from 2 to 36 carbon atoms). The diacid is preferably a dimer resulting from a fatty acid comprising ethylenic unsaturation having at least 16 carbon atoms, preferably from 16 to 24 carbon atoms, such as oleic acid, linoleic acid or linolenic acid. The diamine is preferably ethylenediamine, hexylenediamine or hexamethylenediamine. The triamine is, for example, ethylenetriamine. For the polymers comprising one or two end carboxylic acid groups, it is advantageous to esterify them with a monoalcohol having at least 4 carbon atoms, preferably from 10 to 36 carbon atoms and better still from 12 to 24 carbon atoms and even better still from 16 to 24 carbon atoms, for example 18 carbon atoms.

The lipophilic polyamide polycondensate of the composition according to the invention can be chosen in particular from polymers of following formula (A):

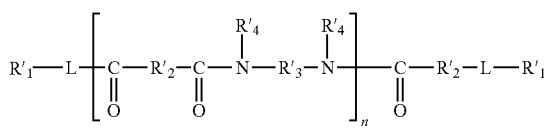

(A)

in which:

n is an integer ranging from 1 to 30, $R'_1$ independently represents, in each case, a fatty chain and is chosen from an alkyl or alkenyl group having at least one carbon atom and in particular from 4 to 24 carbon atoms;

$R'_2$ independently represents, in each case, a hydrocarbon radical comprising from 1 to 52 carbon atoms;

$R'_3$ independently represents, in each case, an organic group comprising at least one atom chosen from carbon, hydrogen or nitrogen atoms, provided that $R'_3$ comprises at least 3 carbon atoms;

$R'_4$ independently represents, in each case: a hydrogen atom, an alkyl group comprising from 1 to 10 carbon atoms or a direct bond to at least one group chosen from $R'_3$ and another $R'_4$, so that, when the said group is another $R'_4$, the nitrogen atom to which both $R'_3$ and $R'_4$ are bonded forms part of a heterocyclic structure defined by $R'_4$—N—$R'_3$, provided that at least 50% of the $R'_4$ groups represent a hydrogen atom, and L represents a bonding group, preferably chosen from ester, ether, amine, urea, urethane, thioester, thioether, thiourea or thiourethane, optionally substituted by at least one $R'_1$ group as defined above.

According to one embodiment, these polymers are chosen from the polymers of formula (A) in which the bonding group L represents an ester group

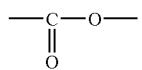

These polymers are more especially those described in the document U.S. Pat. No. 5,783,657 of Union Camp.

Each of these polymers satisfies in particular the following formula (B):

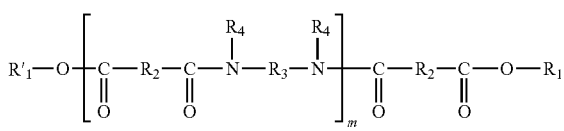

(B)

in which:

m denotes an integral number of amide units such that the number of ester groups represents from 10% to 50% of the total number of the ester and amide groups;

$R_1$ is in each case independently an alkyl or alkenyl group having at least 4 carbon atoms and in particular from 4 to 24 carbon atoms;

$R_2$ independently represents, in each case, a $C_4$ to $C_{42}$ hydrocarbon group, provided that 50% of the $R_2$ groups represent a $C_{30}$ to $C_{42}$ hydrocarbon group;

$R_3$ independently represents, in each case, an organic group provided with at least two carbon atoms, with hydrogen atoms and optionally with one or more oxygen or nitrogen atoms;

and $R_4$ independently represents, in each case, a hydrogen atom, a $C_1$ to $C_{10}$ alkyl group or a direct bond to $R_3$ or to another $R_4$, so that the nitrogen atom to which both $R_3$ and $R_4$ are bonded forms part of a heterocyclic structure defined by $R_4$—N—$R_3$, with at least 50% of the $R_4$ groups representing a hydrogen atom.

In the specific case of the formula (B), the optionally functionalized end fatty chains within the meaning of the invention are end chains bonded to the final nitrogen atom of the polyamide backbone.

In particular, the ester groups of the formula (B), which form part of the end and/or pendent fatty chains within the meaning of the invention, represent from 15 to 40% of the total number of ester and amide groups and better still from 20 to 35%.

Furthermore, m advantageously represents an integer ranging from 1 to 5 and better still of greater than 2.

Preferably, $R_1$ is a $C_{12}$ to $C_{22}$ and preferably $C_{16}$ to $C_{22}$ alkyl group. Advantageously, $R_2$ can be a $C_{10}$ to $C_{42}$ hydrocarbon (alkylene) group. Preferably, at least 50% and better still at least 75% of the $R_2$ groups are groups having from 30 to 42 carbon atoms. The other $R_2$ groups are hydrogenated $C_4$ to $C_{19}$ and even $C_4$ to $C_{12}$ groups.

Preferably, $R_3$ represents a $C_2$ to $C_{36}$ hydrocarbon group or a polyoxyalkylene group and $R_4$ represents a hydrogen atom. Preferably, $R_3$ represents a $C_2$ to $C_{12}$ hydrocarbon group.

The hydrocarbon groups can be saturated or unsaturated and linear, cyclic or branched groups. Furthermore, the alkyl and alkylene groups can be saturated or unsaturated and linear or branched groups.

Generally, the polymers of formula (B) are provided in the form of blends of polymers, it being possible for these blends to additionally comprise a synthetic product corresponding to a compound of formula (B) where n has the value 0, that is to say a diester.

According to a particularly preferred form of the invention, use will be made of a blend of copolymers of a $C_{36}$ diacid condensed with ethylenediamine; the end ester groups result from the esterification of the remaining acid endings by cetyl alcohol, stearyl alcohol or their mixtures (also known as cetearyl alcohol) (INCI name: Ethylenediamine/Stearyl Dimer Dilinoleate Copolymer). Its weight-average molecular weight is preferably 6000. These blends are sold in particular by Arizona Chemical under the trade names Uniclear 80 and Uniclear 100 VG respectively in the form of an 80% (as active material) gel in a mineral oil and of a 100% (as active material) gel. They have a softening point from 88° C. to 94° C.

Mention may also be made, as polyamide polycondensates corresponding to the general formula (A), of polymers comprising at least one end fatty chain bonded to the polymeric backbone via at least one tertiary amide bonding group (also known as amide terminated polyamide or ATPA). Reference may be made, for further information on these polymers, to the document U.S. Pat. No. 6,503,522.

According to a particularly preferred form of the invention, use will more particularly be made of a copolymer of hydrogenated dilinoleic acid, ethylene-diamine and di($C_{14}$-$C_{18}$) alkylamine(s) (INCI name: Ethylenediamide/Hydrogenated Dimer Dilinoleate Copolymer Bis-Di-$C_{14}$-$C_{18}$ Alkyl Amide). This copolymer is sold in particular under the trade name Sylvaclear A200V by Arizona Chemical.

According to another embodiment, the polyamide of formula (A) can also be a poly(ester-amide) comprising ester ends (ester-terminated poly(ester-amide) or ETPEA), such as, for example, those whose preparation is described in the document U.S. Pat. No. 6,552,160.

According to a particularly preferred form of the invention, use will more particularly be made of a copolymer of hydrogenated dilinoleic acid, ethylenediamine, neopentyl glycol and stearyl alcohol (INCI name: Bis-Stearyl Ethylenediamine/Neopentyl Glycol/Stearyl Hydrogenated Dimer Dilinoleate Copolymer). This copolymer is sold in particular under the trade name Sylvaclear C75 V by Arizona Chemical.

Mention may also be made, as polyamide polycondensates which can be used in the invention, of those comprising at least one end fatty chain bonded to the polymeric backbone via at least one ether or polyether bonding group (it is then said to be an ether terminated poly(ether)amide). Such polymers are described, for example, in the document U.S. Pat. No. 6,399,713.

The polyamides in accordance with the invention advantageously have a softening point of greater than 65° C. which can range up to 190° C. Preferably, it exhibits a softening point ranging from 70 to 130° C. and better still from 80 to 105° C. The polyamide is in particular a nonwaxy polymer.

Mention may also be made, as polyamide polycondensates which can be used in the invention, of polyamide resins resulting from the condensation of an aliphatic dicarboxylic acid and of a diamine (including the compounds having more than 2 carbonyl groups and 2 amine groups), the carbonyl and amine groups of adjacent whole units being condensed via an amide bond. These polyamide resins are in particular those sold under the Versamid® trademark by General Mills, Inc. and Henkel Corp. (Versamid 930, 744 or 1655) or under the Onamid® trademark, in particular Onamid S or C, by Olin Mathieson Chemical Corp. These resins have a weight-average molecular weight ranging from 6000 to 9000. Reference may be made, for further information on these polyamides, to the documents U.S. Pat. No. 3,645,705 and U.S. Pat. No. 3,148,125. More especially, Versamid® 930 or 744 is used.

Use may also be made of the polyamides sold by Arizona Chemical under the Uni-Rez references (2658, 2931, 2970, 2621, 2613, 2624, 2665, 1554, 2623, 2662) and of the product sold under the reference Macromelt 6212 by Henkel. Reference may be made, for further information on these polyamides, to the document U.S. Pat. No. 5,500,209.

It is also possible to use polyamide resins resulting from vegetables, such as those described in U.S. Pat. No. 5,783,657 and U.S. Pat. No. 5,998,570.

Hydrocarbon Oils

The compositions of the invention comprise at least one hydrocarbon oil which can be volatile or non-volatile.

"Volatile oil" is understood to mean, within the meaning of the invention, an oil capable of evaporating on contact with the skin or the keratinous fibre in less than one hour at ambient temperature and atmospheric pressure. The volatile oil or oils of the invention are volatile cosmetic oils which are liquid at ambient temperature and which have a non zero vapour pressure, at ambient temperature and atmospheric pressure, ranging in particular from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

"Nonvolatile oil" is understood to mean an oil which remains on the skin or the keratinous fibre at ambient temperature and atmospheric pressure for at least several hours and which has in particular a vapour pressure of less than $10^{-3}$ mmHg) (0.13 Pa).

The hydrocarbon oil or oils are preferably present in the composition of the invention at concentrations ranging from 30 to 99.8% by weight and more preferably from 40 to 90% by weight, with respect to the total weight of the composition.

Mention may in particular be made, as non-volatile hydrocarbon oils which can be used according to the invention, of:

(i) hydrocarbon oils of vegetable origin, such as glyceride triesters, which are generally triesters of fatty acids and of glycerol, the fatty acids of which can have varied chain lengths from $C_4$ to $C_{24}$, it being possible for these chains to be linear or branched and saturated or unsaturated; these oils are in particular wheat germ, sunflower, grape seed, sesame, maize, apricot, castor, shea, avocado, olive, soybean, sweet almond, palm, rapeseed, cottonseed, hazelnut, macadamia, jojoba, alfalfa, poppy, pumpkinseed, marrow, blackcurrant seed, evening primrose, millet, barley, quinoa, rye, safflower, passion flower or musk rose oil; or also triglycerides of caprylic/capric acids, such as those sold by Stéarineries Dubois or those sold under the names Miglyol 810, 812 and 818 by Dynamit Nobel, ii) synthetic ethers having from 10 to 40 carbon atoms;

iii) linear or branched hydrocarbons of mineral or synthetic origin, such as liquid petrolatum, polydecenes, hydrogenated polyisobutene, such as Parleam, squalane and their mixtures;

iv) synthetic esters, such as the oils of formula RCOOR' in which R represents the residue of a linear or branched fatty acid comprising from 1 to 40 carbon atoms and R' represents a hydrocarbon chain, in particular a branched hydrocarbon chain, comprising from 1 to 40 carbon atoms, provided that R+R' is ≥10, such as, for example, Purcellin oil (cetearyl octanoate), isopropyl myristate, isopropyl palmitate, $C_{12}$-$C_{15}$ alkyl benzoate, such as the product sold under the trade name "Finsolu TN" or "Witconol TN" by Witco or "Tegosoft TN" by Evonik Goldschmidt, 2-ethylphenyl benzoate, such as the commercial product sold under the name "X-Tend 226" by ISP, isopropyl lanolate, hexyl laurate, diisopropyl adipate, isononyl isononanoate, oleyl erucate, 2-ethylhexyl palmitate, isostearyl isostearate, or octanoates, decanoates or ricinoleates of alcohols or polyalcohols, such as propylene glycol dioctanoate; hydroxylated esters, such as isostearyl lactate or diisostearyl malate; pentaerythritol esters; citrates or tartrates, such as di(linear $C_{12}$-$C_{13}$ alkyl) tartrates, such as those sold under the name Cosmacol ETI by Enichem Augusta Industriale, and di(linear $C_{14-15}$alkyl) tartrates, such as those sold under the name Cosmacol ETL by the same company; or acetates.

v) fatty alcohols comprising a branched and/or unsaturated carbon chain having from 12 to 26 carbon atoms which are liquid at ambient temperature, such as octyldodecanol, isostearyl alcohol, oleyl alcohol, 2-hexyldecanol, 2-butyloctanol or 2-undecylpentadecanol;

(vi) higher fatty acids, such as oleic acid, linoleic acid or linolenic acid;

(vii) carbonates, such as dicaprylyl carbonate, for example the product sold under the name "Cetiol CC" by Cognis;

(viii) fatty amides, such as isopropyl N-lauroyl sarcosinate, for example the product sold under the trade name Eldew SL205 by Ajinomoto;

and their mixtures.

Volatile hydrocarbon oils can be chosen from hydrocarbon oils having from 8 to 16 carbon atoms, in particular branched $C_8$-$C_{16}$ alkanes, such as $C_8$-$C_{16}$ isoalkanes of petroleum origin (also known as isoparaffins), such as isododecane (also known as 2,2,4,4,6-pentamethylheptane), isododecane, isohexadecane or the oils sold under the Isopars or Permethyls trade names, branched $C_8$-$C_{16}$ esters, isohexyl neopentanoate, and their mixtures. Other volatile hydrocarbon oils, such as petroleum distillates, in particular those sold under the name Shell Solt by Shell, can also be used. According to one embodiment, the volatile solvent is chosen from volatile hydrocarbon oils having from 8 to 16 carbon atoms and their mixtures.

Mention may also be made of the alkanes described in the patent applications from Cognis WO 2007/068371 or WO 2008/155059 (mixtures of distinct alkanes differing by at least one carbon). These alkanes are obtained from fatty alcohols, themselves obtained from coconut oil or palm oil. Mention may be made of the mixtures of n-undecane ($C_{11}$) and n-tridecane ($C_{13}$) obtained in Examples 1 and 2 of Application WO 2008/155059 from Cognis. Mention may also be made of the n-dodecane ($C_{12}$) and the n-tetradecane ($C_{14}$) respectively sold by Sasol under the references Parafol 12-97 and Parafol 14-97, and their mixtures.

Preference will more particularly be given, among hydrocarbon oils which can be used according to the invention, to glyceride triesters and in particular the triglycerides of caprylic/capric acids, synthetic esters, in particular isononyl isononanoate, oleyl erucate or $C_{12}$-$C_{15}$ alkyl benzoate, and fatty alcohols, in particular octyldodecanol.

Additional Oils

The compositions according to the invention can furthermore comprise one or more additional oils which will preferably be chosen from volatile silicone oils or non-volatile silicone oils.

The silicone oil, or oils are present in the liquid fatty phase at concentrations ranging from 0.1 to 20% by weight and preferably from 0.1 to 5% by weight, with respect to the total weight of the liquid fatty phase.

The non-volatile silicone oils can be chosen in particular from polydimethylsiloxanes (PDMSs) which are non-volatile, polydimethylsiloxanes comprising pendent alkyl or alkoxy groups and/or alkyl or alkoxy groups at the end of the silicone chain, groups each having from 2 to 24 carbon atoms, or phenylated silicones, such as phenyl trimethicones, phenyl dimethicones, phenyl(trimethylsiloxy)diphenylsiloxanes, diphenyl dimethicones, diphenyl(methyldiphenyl)trisiloxanes or (2-phenylethyl)trimethylsiloxysilicates.

Mention may be made, as volatile silicone oils, for example, of volatile linear or cyclic silicone oils, in particular those having a viscosity 8 centistokes (8 $10^{-6}$ $m^2$/s) and having in particular from 2 to 7 silicon atoms, these silicones optionally comprising alkyl or alkoxy groups having from 1 to 10 carbon atoms. Mention may in particular be made, as volatile silicone oil which can be used in the invention, of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane, dodecamethylpentasiloxane and their mixtures.

Mention may also be made of the volatile linear alkyltrisiloxane oils of general formula (I):

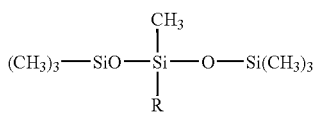

where R represents an alkyl group comprising from 2 to 4 carbon atoms, one or more hydrogen atoms of which can be replaced by a fluorine or chlorine atom.

Mention may be made, among oils of general formula (I), of:
3-butyl-1,1,1,3,5,5,5-heptamethyltrisiloxane,
3-propyl-1,1,1,3,5,5,5-heptamethyltrisiloxane, and
3-ethyl-1,1,1,3,5,5,5-heptamethyltrisiloxane,
corresponding to the oils of formula (I) for which R is respectively a butyl group, a propyl group or an ethyl group.

Linear $C_1$-$C_3$ Monoalcohol

The $C_1$-$C_3$ monoalcohol or monoalcohols present in the compositions of the invention can be chosen from methanol, ethanol, propanol or their mixtures. Ethanol will more particularly be chosen.

They are generally present at concentrations ranging from 0.1 to 40% by weight, more preferably from 2 to 10% by weight, with respect to the total weight of the composition.

Lipophilic Organic UV Screening Agents

They can in particular be chosen from para-aminobenzoic acid derivatives, salicylic derivatives, cinnamic derivatives, benzophenones or aminobenzophenones, anthranilic derivatives, dibenzoylmethane derivatives, β,β-diphenylacrylate derivatives, benzylidenecamphor derivatives, phenylbenzimidazole derivatives, benzotriazole derivatives, triazine derivatives, bisresorcinyltriazines, imidazoline derivatives, benzalmalonate derivatives, 4,4-diarylbutadiene derivatives, benzoxazole derivatives, merocyanines and their mixtures.

Mention may be made, among lipophilic organic UV-A screening agents capable of absorbing UV radiation from 320 to 400 nm, of:

Dibenzoylmethane Derivatives:

4-isopropyldibenzoylmethane, sold under the name of "Eusolex 8020" by Merck, which corresponds to the following formula:

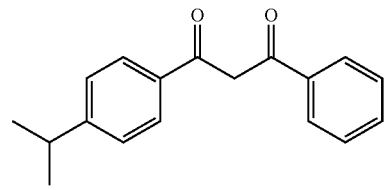 [SMILES: CC(C)c1ccc(C(=O)CC(=O)c2ccccc2)cc1]

1-(4-methoxy-1-benzofuran-5-yl)-3-phenylpropane-1,3-dione, provided for sale by Quest under the name of Pongamol, of formula:

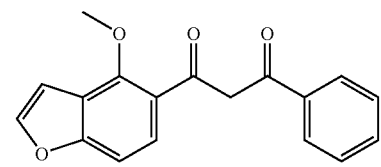 [SMILES: COc1c(C(=O)CC(=O)c2ccccc2)ccc2occc12]

1-(4-(tert-butyl)phenyl)-3-(2-hydroxyphenyl)propane-1,3-dione, of formula:

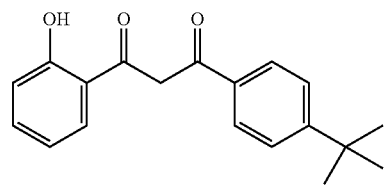 [SMILES: CC(C)(C)c1ccc(C(=O)CC(=O)c2ccccc2O)cc1]

Butyl Methoxydibenzoylmethane, sold in particular under the trade name "Parsol 1789" by Hoffmann-La Roche,
Aminobenzophenones:
n-Hexyl 2-(4-diethylamino-2-hydroxybenzoyl)benzoate, sold under the trade name "Uvinul A+",
Anthranilic Derivatives:
Menthyl anthranilate, sold under the trade name "Neo Heliopan MA" by Haarmann and Reimer,
4,4-Diarylbutadiene Derivatives:
1,1-Dicarboxy-(2,2'-dimethylpropyl)-4,4-diphenylbutadiene.

Those preferred are:
Butyl Methoxydibenzoylmethane
n-Hexyl 2-(4-diethylamino-2-hydroxybenzoyl)benzoate.

Mention may be made, among lipophilic organic UV-B screening agents capable of absorbing UV radiation from 280 to 320 nm, of:
Para-Aminobenzoates:
Ethyl.PABA
Ethyl Dihydroxypropyl PABA
Ethylhexyl Dimethyl PABA (Escalol 507 from ISP)
Salicylic Derivatives:
Homosalate, sold under the name "Eusolex HMS" by Rona/EM Industries,
Ethylhexyl Salicylate, sold under the name "Neo Heliopan OS" by Haarmann and Reimer,
Dipropylene Glycol Salicylate, sold under the name "Dipsal" by Scher,
TEA Salicylate, sold under the name "Neo Heliopan TS" by Haarmann and Reimer,
Cinnamates:
Ethylhexyl Methoxycinnamate, sold in particular under the trade name "Parsol MCX" by Hoffmann-La Roche, Isopropyl Methoxycinnamate,
Isoamyl Methoxycinnamate, sold under the trade name "Neo Heliopan E 1000" by Haarmann and Reimer,
Diisopropyl Methylcinnamate,
Cinoxate,
Glyceryl Ethylhexanoate Dimethoxycinnamate,
β,β'-Diphenylacrylate derivatives:
Octocrylene, sold in particular under the trade name "Uvinul N539" by BASF,
Etocrylene, sold in particular under the trade name "Uvinul N35" by BASF,
Benyzlidenecamphor Derivatives:
3-Benzylidenecamphor, manufactured under the name "Mexoryl SD" by Chimex,
Methylbenzylidenecamphor, sold under the name "Eusolex 6300" by Merck,
Polyacrylamidomethyl BenzylideneCamphor, manufactured under the name "Mexoryl SW" by Chimex,
Triazine Derivatives:
Ethylhexyl triazone, sold in particular under the trade name "Uvinul T150" by BASF,
2,4,6-Tris(dineopentyl 4'-aminobenzalmalonate)-s-triazine,
2,4,6-Tris(diisobutyl 4'-aminobenzalmalonate)-s-triazine,
2,4-Bis(dineopentyl 4'-aminobenzalmalonate)-6-(n-butyl 4'-aminobenzoate)-s-triazine,
2,4-Bis(n-butyl 4'-aminobenzoate)-6-(aminopropyltrisiloxane)-s-triazine,
Imidazoline Derivatives:
Ethylhexyl Dimethoxybenzylidene Dioxoimidazoline Propionate,
Benzalmalonate Derivatives:
Polyorganosiloxanes comprising a benzalmalonate functional group, such as Polysilicone-15, sold under the trade name "Parsol SLX" by Hoffmann-La Roche, Dineopentyl 4'-methoxybenzalmalonate,
Merocyanine Derivatives:
Octyl 5-N,N-diethylamino-2-phenylsulphonyl-2,4-pentadienoate.

The preferred ones are
Homosalate
Ethylhexyl Salicylate
Ethylhexyl Methoxycinnamate
Octocrylene
Ethylhexyl Triazone
2,4-Bis(n-butyl 4'-aminobenzoate)-6-(aminopropyl-trisiloxane)-s-triazine,
Octyl 5-N,N-diethylamino-2-phenylsulphonyl-2,4-pentadienoate.

Mention may be made, among broad-spectrum lipophilic organic screening agents capable of absorbing UV-A and UV-B radiation, of:
Benzophenone Derivatives:
Benzophenone-1, sold under the trade name "Uvinul 400" by BASF,
Benzophenone-2, sold under the trade name "Uvinul D50" by BASF,
Benzophenone-3 or Oxybenzone, sold under the trade name "Uvinul M40" by BASF,
Benzophenone-5,
Benzophenone-6, sold under the trade name "Helisorb 11" by Norquay,
Benzophenone-8, sold under the trade name "Spectra-Sorb UV-24" by American Cyanamid,
Benzophenone-10,
Benzophenone-11,
Benzophenone-12,
Benzotriazole Derivatives:
Drometrizole Trisiloxane, sold under the name "Silatrizole" by Rhodia Chimie,
Bumetrizole, sold under the name "Tinoguard AS" by Ciba-Geigy,
Bisresorcinyltriazine Derivatives:
Bis-Ethylhexyloxyphenol Methoxyphenyl Triazine, sold under the trade name "Tinosorb S" by Ciba Geigy,
Benzoxazole Derivatives:
2,4-Bis[5-1(dimethylpropyl)benzoxazol-2-yl-(4-phenyl)imino]-6-(2-ethylhexyl)imino-1,3,5-triazine, sold under the name of Uvasorb K2A by Sigma 3V.

The preferred ones are:
Benzophenone-3
Drometrizole Trisiloxane
Bis-Ethylhexyloxyphenol Methoxyphenyl Triazine.

The lipophilic organic screening agents are generally present in the compositions according to the invention in proportions ranging from 0.1 to 50% by weight, with respect to the total weight of the composition, and preferably ranging from 2 to 30% by weight, with respect to the total weight of the composition.

According to a particularly preferred form of the invention, the compositions will be transparent and will preferably exhibit a turbidity of less than 1000 NTU (Nephelometric Turbidity Units) at 25° C., preferably of less than 50 NTU at 25° C. and more preferably still of less than 15 NTU, measured with a 2100P Turbidimeter device from HACH. (to be confirmed).

According to a particularly preferred form of the invention, the compositions will exhibit an SPF of greater than 10, even of greater than 15 and even of greater than 20.

According to a particularly preferred form of the invention, the compositions will exhibit a UV-$A_{PPD}$ PF of greater than 5; they subsequently adhere to regulations, in particular to the European regulations, which desire the SPF/PPD ratio to be less than 3.

Additives

The oily composition of the product of the invention can also comprise various additives which may be soluble in the oily phase or be in dispersion in the said oily phase, chosen in particular from lipophilic dyes, lipophilic active principles, lipophilic polymers, other than the polyamide polycondensates of the invention, organic solvents, preservatives, insect repellants, essential oils, fragrances, emollients or propellants.

Mention may be made, among lipophilic cosmetic active principles, for example, of antioxidants; keratolytic agents, such as n-alkylsalicylic acids, for example 5-(n-octanoyl) salicylic acid; vitamins, such as vitamin E (tocopherol and derivatives) or vitamin A (retinol and derivatives); softeners and any lipophilic active agent commonly used in caring for the skin or hair.

Mention may be made, as additional lipophilic polymers, of block copolymers derived from styrene, such as styrene/ethylene-butylene/styrene copolymer, for example the product sold under the name Kraton G-1650E by Kraton Polymers; acrylic or methacrylic acid copolymers, such as the acrylate/stearyl acrylate/dimethicone methacrylate copolymer sold under the name KP 561 P by Shin-Etsu; or Poly-C10-30-Alkyl Acrylates, such as the product sold under the name Interlimer IPA 13-1 by Landec.

Of course, the person skilled in the art will take care to choose the optional additional compound or compounds mentioned above and/or their amounts so that the advantageous properties intrinsically attached to the compositions in accordance with the invention are not, or not substantially, detrimentally affected by the envisaged addition or additions.

Another subject-matter of the present invention is composed of the use of the compositions according to the invention as defined above in the manufacture of products for the cosmetic treatment of the skin, nails, hair, eyelashes, eyebrows and/or scalp, in particular care products or sun protection products.

The cosmetic compositions according to the invention can, for example, be used as care product and/or sun protection product and/or daily photoprotection product and/or makeup product and/or hair product for the face and/or body and/or hair of liquid consistency.

Fragrances

According to a specific form of the invention, the cosmetic compositions according to the invention can constitute scenting products and additionally comprise a scenting substance.

Scenting product is understood to mean any composition which leaves, after application to keratinous substances, a fragrance.

"Scenting substance" is understood to mean any fragrance or aroma capable of scenting human skin and keratinous substances generally comprising the skin, hair, scalp, lips or nails.

Use may be made, as scenting substance, in the composition of the invention, of fragrances and aromas of natural or synthetic origin and their mixtures. Mention may be made, as fragrances and aromas of natural origin, for example, of extracts of flowers (lily, lavender, rose, jasmine, ylang-ylang), of stalks and leaves (patchouli, geranium, bitter orange), of fruits (coriander, anise, cumin, juniper berry), of fruit peels (bergamot, lemon, orange), of roots (angelica, celery, cardamom, iris, sweet flag), of wood (pinewood, sandalwood, guaiac, pink cedar), of grasses and graminae (tarragon, lemon grass, sage, thyme), of needles and branches (spruce, fir, pine, dwarf pine) or of resins and balms (galbanum, elemi, benzoin, myrrh, oliban, opopanax).

Mention may be made, as scenting substance of synthetic origin, for example, of compounds of the ester, ether, aldehyde, ketone, aromatic alcohol and hydrocarbon type.

Mention may in particular be made, as esters, of benzyl acetate, benzyl benzoate, phenoxyethyl isobutyrate, p-(tert-butyl)cyclohexyl acetate, citronellyl acetate, citronellyl formate, geranyl acetate, linalyl acetate, dimethylbenzylcarbinyl acetate, phenylethyl acetate, linalyl benzoate, benzyl formate, ethylmethylphenyl glycinate, alkylcyclohexyl propionate, styrallyl propionate and benzyl salicylate.

Mention may be made, as ethers, of benzyl ethyl ether.

Mention may be made, as aldehydes, for example, of linear alkanals comprising from 8 to 18 carbon atoms, citral, citronellal, citronellyl oxyacetaldehyde, cyclamen aldehyde, hydroxycitronellal, lilial and bourgeonal.

Mention may be made, as ketones, for example, of ionones, such as α-isomethyl ionone, and methyl cedryl ketone.

Mention may be made, among aromatic alcohols and in particular terpene alcohols, of anethol, citronellol, eugenol, isoeugenol, geraniol, linalool, phenylethyl alcohol and terpineol.

Mention may in particular be made, as hydrocarbons, of terpenes. These compounds often exist in the form of mixtures of two or more of these odorous substances.

Furthermore, use may also be made of essential oils, components of aromas, such as, for example, essential oils of sage, camomile, clove, melissa balm, mint, cinnamon tree leaves, lime blossom, juniper, vetiver, olibanum, galbanum, labdanum and lavandin.

Use may be made, as scenting substance, alone or as a mixture, of essential oil of bergamot, dihydromyrcenol, lilial, lyral, citronellol, phenylethyl alcohol, α-hexylcinnamaldehyde, geraniol, benzylacetone, cyclamen aldehyde, linalool, ambroxan, indole, hedione, sandelice, essential oils of lemon, of mandarin and of orange, allylamine glycolate, cyclovertal, essential oil of lavandin, essential oil of sage, beta-damascone, essential oil of geranium, cyclohexyl salicylate, phenylacetic acid, geranyl acetate, benzyl acetate or rose oxide.

Use may also be made of a mixture of different scenting substances which together produce an agreeable note for the user. Mention may be made, among known olfactory notes, for example, of hesperidic fragrances, aromatic ones, floral fragrances, musky ones, fruity fragrances, spicy ones, oriental fragrances, sea fragrances, aquatic notes, chypre fragrances, woody fragrances, fougere ones and their mixtures.

The amount of scenting substance(s) will preferably be 5 to 25% by weight, better still from 10 to 20% by weight, with respect to the total weight of the composition.

Additional Colouring Agents

According to another specific form of the invention, the compositions of the invention can furthermore comprise one or more additional colouring agents.

The additional colouring agents can also be chosen from synthetic or natural direct dyes. They can be organic or inorganic dyes.

The synthetic or natural fat-soluble organic dyes are, for example, DC Red 17, DC Red 21, DC Red 27, DC Green 6, DC Yellow 11, DC Violet 2, DC Orange 5, Sudan red, carotenes (β-carotene, lycopene), xanthophylls (capsanthin, capsorubin, lutein), palm oil, Sudan brown, quinoline yellow, annatto or curcumin.

The additional colouring agents can also be chosen from particulate colouring materials which are preferably chosen from pigments, pearlescent agents or interference pigments, or glitter.

Pigments should be understood as meaning white or coloured and inorganic or organic particles of any shape which are insoluble in the physiological medium and which are intended to colour the composition.

The pigments can be white or coloured and inorganic and/or organic. Mention may be made, among inorganic pigments, of titanium dioxide, which is optionally surface-treated, zirconium or cerium oxides, and zinc, iron (black, yellow or red) or chromium oxides, manganese violet, ultramarine blue, chromium hydrate, ferric blue or metal powders, such as aluminium powder or copper powder.

Mention may be made, among organic pigments, of carbon black, pigments of D & C type and lakes, based on cochineal carmine, of barium, strontium, calcium or aluminium.

Mention may also be made of effect pigments, such as particles comprising an organic or inorganic and natural or synthetic substrate, for example glass, acrylic resins, polyester, polyurethane, polyethylene terephthalate, ceramics or aluminas, the said substrate being or not being covered with metallic substances, such as aluminium, gold, silver, platinum, copper or bronze, or with metal oxides, such as titanium dioxide, iron oxide, chromium oxide and their mixtures.

Within the meaning of the present invention, the expression "interference particles or pearlescent agents" denotes any particle generally having a multilayer structure such that it makes possible the creation of an effect of colour by interference of the light rays which diffract and scatter differently according to the nature of the layers. The colouring effects obtained are related to the lamellar structure of these particles and derive from the physical laws of the optics of thin layers (see: Pearl Lustre Pigments—Physical principles, properties, applications—R. Maisch and M. Weigand. Verlag Moderne Industrie). Thus, these particles can exhibit colours which vary according to the angle of observation and the incidence of the light.

Within the meaning of the present invention, a multilayer structure is intended to denote, without distinction, a structure formed of a substrate covered with a single layer or a structure formed of a substrate covered with at least two, indeed even several, consecutive layers.

The multilayer structure can thus comprise one layer, indeed even at least two layers, each layer, independently or not of the other layer(s), being made of at least one material chosen from the group consisting of the following materials: $MgF_2$, $CeF_3$, ZnS, ZnSe, Si, $SiO_2$, Ge, Te, $Fe_2O_3$, Pt, Va, $Al_2O_3$, MgO, $Y_2O_3$, $S_2O_3$, SiO, $HfO_2$, $ZrO_2$, $CeO_2$, $Nb_2O_5$, $Ta_2O_5$, $TiO_2$, Ag, Al, Au, Cu, Rb, Ti, Ta, W, Zn, $MoS_2$, cryolite, alloys, polymers and their combinations.

Generally, the multilayer structure is of inorganic nature.

More particularly, the interference particles under consideration according to the invention can be interference pigments or also natural or synthetic and monolayer or multilayer pearlescent agents, in particular formed of a natural substrate based, inter alia, on mica which is covered with one or more layers of metal oxide.

The interference particles according to the invention are characterized in that 50% of the population by weight has a diameter ($d_{50}$) of less than 40 µm, more particularly of less than 30 µm, in particular of less than 20 µm and especially of less than 15 µm, measured with a laser particle sizer, such as, for example, the Mastersizer 2000® from Malvernet or the BI90+® from Brookhaven Instrument Corporation.

The pearlescent agents of mica/tin oxide/titanium oxide type, such as, for example, those sold under the names Timiron Silk Blue®, Timiron Silk Red®, Timiron Silk Green®, Timiron Silk Gold® and Timiron Super Silk® by Merck, and mica/iron oxide/titanium oxide pearlescent agents, such as, for example, Flamenco Satin Blue®, Flamenco Satin Red®, Flamenco Satin Violet® and Flamenco Orange 320C provided by Engelhard, and their mixtures, are very particularly suitable for the invention.

More specifically, these pigments can be present in amounts ranging from 0.01 to, 10% by weight and preferably ranging from 0.1 to 5% by weight, with respect to the total weight of the composition.

Vapourisable Compositions

The compositions according to the invention can be provided in the form of a vapourisable oil applied to the skin or hair in the form of fine particles by means of pressurisation devices. The devices in accordance with the invention are well known to a person skilled in the art and comprise nonaerosol pumps or "atomisers", aerosol containers comprising a propellant and aerosol pumps using compressed air as propellant. The latter are described in U.S. Pat. No. 4,077,441 and U.S. Pat. No. 4,850,517 (forming an integral part of the content of the description).

These compositions can also be impregnated on supports of wipe type or they can be packaged as lotions in bottles with a reducer.

The compositions packaged in aerosols in accordance with the invention generally comprise conventional propellants, such as, for example, hydrofluorinated compounds, dichlorodifluoromethane, difluoroethane, dimethyl ether, isobutane, n-butane, propane or trichlorofluoromethane. They are preferably present in amounts ranging from 15 to 50% by weight, with respect to the total weight of the composition.

Concrete but in no way limiting examples illustrating the invention will now be given.

EXAMPLES 5 anhydrous Formulation Examples 1 to 5 were prepared. The amounts are expressed as % by weight, with respect to the total weight of the composition.

| Phase | Ingredients | Example 1 (outside the invention) |
|---|---|---|
| A | Paraffinum liquidum | 29.4 |
|   | Caprylic/capric triglyceride (60/40) (Myritol 318, Cognis) | 20.0 |
|   | Ethylhexyl methoxycinnamate | 7.5 |
|   | Drometrizole trisiloxane | 2.5 |
|   | Fragrance | 0.5 |
|   | Vitamin E | 0.2 |
|   | Dye | 0.004 |
| B | Cyclopentasiloxane | q.s. for |

| Phase | Ingredients | Example 2 (outside the invention) |
|---|---|---|
| A | Ethylenediamine/stearyl dimer dilinoleate copolymer (Uniclear 100 VG, Arizona Chemical) | 5 |
|   | Caprylic/capric triglyceride (60/40) (Myritol 318, | 39 |

-continued

| | | | | |
|---|---|---|---|---|
| | Cognis) | | | |
| | Butyl methoxydibenzoylmethane | | 2 | |
| | Ethylhexyl triazone | | 5 | |
| | Octocrylene | | 9 | |
| | C12-15 Alkyl benzoate (Tegosoft TN from Evonik Goldschmidt) | | 10 | |
| B | 2-Octyldodecanol | | q.s. for | |

| Phase | Ingredients | Ex. 3 | Ex. 4 | Ex. 5 |
|---|---|---|---|---|
| A | Ethylenediamine/stearyl dimer dilinoleate copolymer (Uniclear 100 VG, Arizona Chemical) | 6 | 6 | — |
| | Ethylenediamine/hydrogenated dimer dilinoleate copolymer bis-di-C14-18 alkyl amide | — | — | 6 |
| | Caprylic/capric triglyceride (60/40) (Myritol 318, Cognis) | 33 | 33 | 33 |
| | Butyl methoxydibenzoylmethane | 4 | 4 | 4 |
| | Ethylhexyl triazone | 3 | 3 | 3 |
| | Octocrylene | 5 | 5 | 5 |
| | Ethylhexyl salicylate | — | 5 | — |
| | Drometrizole trisiloxane | 1 | 1 | 1 |
| | Bis-ethylhexyloxyphenol methoxyphenyl triazine | — | 3 | — |
| | C12-15 Alkyl benzoate (Tegosoft TN from Evonik Goldschmidt) | 13 | 13 | 13 |
| | 2-Octyldodecanol | q.s. for | q.s. for | q.s. for |
| | Fragrance | 0.5 | 0.5 | 0.5 |
| | Dye | 0.004 | 0.004 | 0.004 |
| | Vitamin E | 0.5 | 0.5 | 0.5 |
| B | Ethanol | 5 | 5 | 5 |

The procedure for the compositions 1 to 5 is as follows:

The phase A is prepared by mixing the starting materials and the mixture is heated at 90-95° C. with stirring until the starting materials have completely dissolved. The mixture is cooled to 25° C. with stirring. The phase B is subsequently incorporated at 25° C. with stirring until the mixture is completely homogeneous.

The following are evaluated for each of the compositions:
(1) the viscosity, measured using a Rheomat 180 viscometer at 25° C. at a rotation speed of 200 rpm after rotating for 30 seconds
(2) the stability at 2 months at 4, 25 and 45° C.
(3) the appearance of the composition after 24 hours
(4) the in vivo SPF on 5 subjects according to the international method published by Colipa/CTFA SA/JCIA (May 2006)
(5) the UV-$A_{PPD}$ PF on 5 subjects according to the recommendations of the JCIA (version of Nov. 15, 1995).

The results are shown in the following Tables 1 and 2:

TABLE 1

| | Examples | |
|---|---|---|
| | Ex. 1 (outside the invention) | Ex. 2 (outside the invention) |
| Controls at 24 hours | viscosity = 0.0035 Pa · s Liquid transparent oil 1.3 NTU | viscosity = 0.65 Pa · s Thick oily gel which does not flow 2.3 NTU |
| Stability after storing for 2 months at 4, 25 and 45° C. | Stable | Heterogeneous appearance with exudation of oil: presence of gelled and ungelled parts |
| Effectiveness in vivo SPF | 7.2 (5 subjects) | Unmeasurable |
| in vivo UV-$A_{PPD}$ PF | 3.0 (5 subjects) | Unmeasurable |

TABLE 2

| | | Examples | | |
|---|---|---|---|---|
| | | Ex. 3 (invention) | Ex. 4 (invention) | Ex. 5 (invention) |
| Controls at 24 hours | | viscosity = 0.024 Pa · s Liquid transparent oil 13 NTU | viscosity = 0.026 Pa · s Liquid transparent oil 5.8 NTU | viscosity = 0.025 Pa · s Liquid transparent oil 2.6 NTU |
| Stability after storing for 2 months at 4, 25 and 45° C. | | Stable and of the same order as the controls at 24 h | Stable and of the same order as the controls at 24 h | Stable and of the same order as the controls at 24 h |
| Effectiveness | in vivo SPF | 20.2 | 23.8 | 24.2 |
| | in vivo UV-$A_{PPD}$ PF | 11.8 | >5 | 15.4 |

These oils are thus stable on storage after 2 months at different temperatures (4, 25, 45° C.) They exhibit the advantage of being vapourisable and cosmetically pleasing. The SPF values achieved are greater than 15, in contrast to Examples 1 and 2.

The invention claimed is:

1. An anhydrous fluid composition comprising, in a cosmetically acceptable medium:
   a) at least one hydrocarbon oil and
   b) at least one lipophilic organic UV screening agent and
   c) at least one linear $C_1$-$C_3$ monoalcohol and
   d) at least one lipophilic polyamide polycondensate chosen from the polymers of the following formula (A):

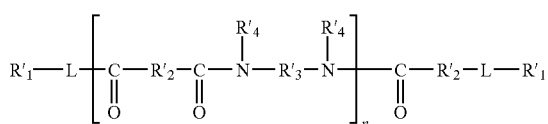

(A)

In which:
n is an integer ranging from 1 to 30,
$R'_1$ independently represents, in each case, a fatty chain and is chosen from an alkyl or alkenyl group having at least one carbon atom and in particular from 4 to 24 carbon atoms;

R'$_2$ independently represents, in each case, a hydrocarbon radical comprising from 1 to 52 carbon atoms;

R'$_3$ independently represents, in each case, an organic group comprising at least one atom chosen from carbon, hydrogen or nitrogen atoms, provided that R'3 comprises at least 3 carbon atoms;

R'$_4$ independently represents, in each case: a hydrogen atom, an alkyl group comprising from 1 to 10 carbon atoms or a direct bond to at least one group chosen from R'$_3$ and another R'$_4$, so that, when the said group is another R'$_4$, the nitrogen atom to which both R'$_3$ and R'$_4$ are bonded forms part of a heterocyclic structure defined by R'$_4$—N—R'$_3$, provided that at least 50% of the R'$_4$ groups represent a hydrogen atom;

L is a tertiary amide bonding group;

Wherein at least one end fatty chain is bonded to the polymeric backbone via at least one tertiary amide bonding group.

2. Composition according to claim 1, where the polycondensate is a copolymer of hydrogenated dilinoleic acid, ethylenediamine and di($C_{14}$-$C_{18}$)alkylamine(s) (INCI name: Ethylenediamide/Hydrogenated Dimer Dilinoleate Copolymer Bis-D$_1$-$C_{14}$-$C_{18}$ Alkyl Amide).

3. The composition according to claim 1, where the hydrocarbon oil or oils at concentrations ranging from 30 to 99.8% by weight with respect to the total weight of the composition.

4. The composition according to claim 1, where the lipophilic organic screening agent or agents are chosen from para-aminobenzoic acid derivatives, salicylic derivatives, cinnamic derivatives, benzophenones or aminobenzophenones, anthranilic derivatives, dibenzoylmethane derivatives, β,β-diphenylacrylate derivatives, benzylidenecamphor derivatives, phenylbenzimidazole derivatives, benzotriazole derivatives, triazine derivatives, bisresorcinyltriazines, imidazoline derivatives, benzalmalonate derivatives, 4,4-diarylbutadiene derivatives, benzoxazole derivatives, merocyanines and their mixtures.

5. The composition according to claim 1, where the linear $C_1$-$C_3$ monoalcohol is ethanol.

6. The composition according to claim 1, characterized in that it is transparent and exhibits a turbidity of less than 1000 NTU at 25° C.

7. The Composition according to claim 1, characterized in that it exhibits an SPF of greater than 10.

8. The composition according to claim 1, characterized in that it exhibits a UV-A$_{PPD}$ PF of greater than 5 and/or an SPF/PPD ratio of less than 3.

9. The composition according to claim 1 wherein L represents a bonding group chosen from ester, ether, amine, urea, urethane, thioester, thioether, thiourea or thiourethane, optionally substituted by at least one R'$_1$ group.

10. The composition according to claim 1, where the hydrocarbon oil or oils at concentrations ranging from 40 to 90% by weight, with respect to the total weight of the composition.

11. The composition according to claim 1, where the linear $C_1$-$C_3$ monoalcohol is present in the composition at a concentration from 0.1 to 40% by weight with respect to the total weight of the composition.

12. The composition according to claim 1, where the linear $C_1$-$C_3$ monoalcohol is present in the composition at a concentration from 2 to 10% by weight with respect to the total weight of the composition.

13. The composition according to claim 12, where the linear $C_1$-$C_3$ monoalcohol is ethanol.

14. The composition according to claim 13, characterized in that it is transparent and exhibits a turbidity of less than 50 NTU at 25° C.

15. The composition according to claim 1, characterized in that it is transparent and exhibits a turbidity of less than 50 NTU at 25° C.

16. The composition according to claim 1, characterized in that it is transparent and exhibits a turbidity of less than 15 NTU at 25° C.

17. The composition according to claim 1, having a viscosity of less than 0.5 Pa·s, measured at 25° C. using a Rheomat 180 viscometer at a rotational speed of 200 rpm after rotating for 30 seconds.

\* \* \* \* \*